US00PP14429P39

(12) United States Plant Patent
Pieters

(10) Patent No.: US PP14,429 P3
(45) Date of Patent: Dec. 30, 2003

(54) CHRYSANTHEMUM PLANT NAMED 'GEDI TWO LUC'

(50) Latin Name: *Chrysanthemum morifolium*
Varietal Denomination: Gedi Two Luc

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,809

(22) Filed: May 1, 2002

(65) Prior Publication Data

US 2003/0208810 P1 Nov. 6, 2003

(51) Int. Cl.[7] ..... A01H 5/00
(52) U.S. Cl. ..... Plt./290

(58) Field of Search ..... Plt./287, 290, 289

(56) References Cited

U.S. PATENT DOCUMENTS

PP11,344 P 4/2000 Pieters ..... Plt./290
PP11,569 P 10/2000 Pieters ..... Plt./290

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, Gray-orange ray florets that darken as the inflorescence ages, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Luc'.

BACKGROUND OF THE INVENTION

The new cultivar of hybridization of a female parent Chrysanthemum plant variety 'GEDI VL8' U.S. Plant Pat. No. 11,344) and male parent Chrysanthemum plant variety 'Sapiro Brons' (undistributed in the United States). The new cultivar was discovered and selected by the inventor in October 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Luc' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Luc.' These characteristics in combination distinguish 'Gedi Two Luc' as a new and distinct Chrysanthemum cultivar:

1. Decorative-type inflorescence,
2. Consistent flowering response to short days, blooming consistently after 49 days of short day length,
3. Free branching habit, 4. Gray-orange ray florets that darken as the inflorescence ages,
5. Very uniform round growth habit, and
6. Large quantity of blooms per flowering branch.

Plants of the new cultivar are similar to plants of the female parent variety, 'Gedi VL8' in most horticultural characteristics, however plants of the new cultivar have more blooms per flowering branch, smaller diameter inflorescences, and naturally bloom two weeks earlier than plants of the female parent variety.

Plants of the new cultivar are similar to plants of the male parent variety, 'Sapiro Brons' in most horticultural characteristics, however plants of the new cultivar have a wider diameter inflorescence, more ray florets per inflorescence, and naturally bloom three weeks earlier than plants of the male parent variety.

In comparison to the commercially available variety 'Gedi Oro8 ' (U.S. Plant Pat. No. 11,569), 'Gedi Two Luc' blooms two weeks earlier and has more blooms per flowering branch and many more ray florets per inflorescence.

BRIEF DESCRIPTION OF THE PHOTOGRAPH

The photograph shows a plant of 'Gedi Two Luc' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 95 days from a rooted cutting. The growing temperature ranged from 55° to 68°F. at night to 60° to 75° F. during the day.

Measurements and numerical values represent averages of typical flowering types.

Botanical classification: *Chrysanthemum morifolium* cultivar 'Gedi Two Luc'.
Commercial classification: Garden-type Chrysanthemum.
Parentage: Hybridization of a female parent Chrysanthemum plant variety, 'GEDI VL8' (U.S. Plant Pat. No. 11,344), and a male parent Chrysanthemum plant variety 'Sapiro Brons' (undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 20 cm.
Spread: Approximately 18 cm.
Growth rate: Moderate.
Branching characteristics: Free Branching.
Length of lateral branches: Approximately 18 cm.
Number of leaves per lateral branch: Approximately 14.

FOLIAGE

Leaf:
- *Arrangement.*—Alternate.
- *Average length.*—Approximately 7.2 cm.
- *Average width.*—Approximately 3.5 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 137C. Mature foliage upper side: Near 137A. Mature foliage under side: Near 137C. Venation upper side: Near 138C. Venation under side: Near 138B.
- *Venation type.*—Palmately net.

Petiole:
- *Average length.*—Approximately 2.1 cm.
- *Color.*—Near 138B.
- *Diameter.*—Approximately 0.25 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last two weeks of September.
- *Number of inflorescences per lateral branch.*—Approximately 32.
- *Inflorescence diameter.*—Approximately 4.5 cm.
- *Inflorescence depth.*—Approximately 1.5 cm.
- *Inflorescence longevity on plant.*—Approximately 28 days.
- *Persistence.*—Persistent.

Ray florets:
- *Appearance.*—Matte.
- *Texture.*—Smooth.
- *Average number per flower.*—203.
- *Shape.*—Oblong.
- *Margin.*—Entire.
- *Apex.*—Retuse.
- *Length.*—Approximately 1.6 cm.
- *Width.*—Approximately 0.5 cm.
- *Color.*—Upper surface at first opening: outer ray florets: Near 167A. Inner ray florets: Near 1B. Upper surface at maturity: Near 163A. Upper surface at fading: Near 171B. Under surface at first opening: Near 164A. Under surface at maturity: Near 174C. Under surface at fading: Near 166C.

Disc florets: Not present.

Peduncle:
- *Length.*—At terminal end (shortest): Approximately 4.6 cm. At lateral end (longest): Approximately 7.6 cm.
- *Angle to stem.*—Acute.
- *Strength.*—Moderate.
- *Color.*—Near 138B.
- *Habit.*—Upright.
- *Diameter.*—Approximately 0.2 cm.
- *Surface texture.*—Lightly pubescent.

Inflorescence bud:
- *Length.*—Approximately 1 cm.
- *Diameter.*—Approximately 0.9 cm.
- *Form.*—Globular.
- *Color (when ray florets first begin to emerge).*—Near 172B.

Involucral bracts (phyllaries):
- *Appearance.*—Matte.
- *Texture.*—Lightly pubescent.
- *Number.*—Approximately 104.
- *Shape.*—Oblanceolate.
- *Margin.*—Entire.
- *Apex.*—Acute.
- *Length.*—Approximately 0.7 cm.
- *Width.*—Approximately 0.2 cm.
- *Color.*—Upper side: Near 136A.

REPRODUCTIVE ORGANS

Ray florets:
- *Number of pistils per flower.*—1.
- *Stigma shape.*—2 branched.
- *Stigma color.*—Near 7A.
- *Style color.*—Near 154D.
- *Style length.*—Approximately 0.4 cm.
- *Stamens.*—Absent.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Luc' as herein illustrated and described.

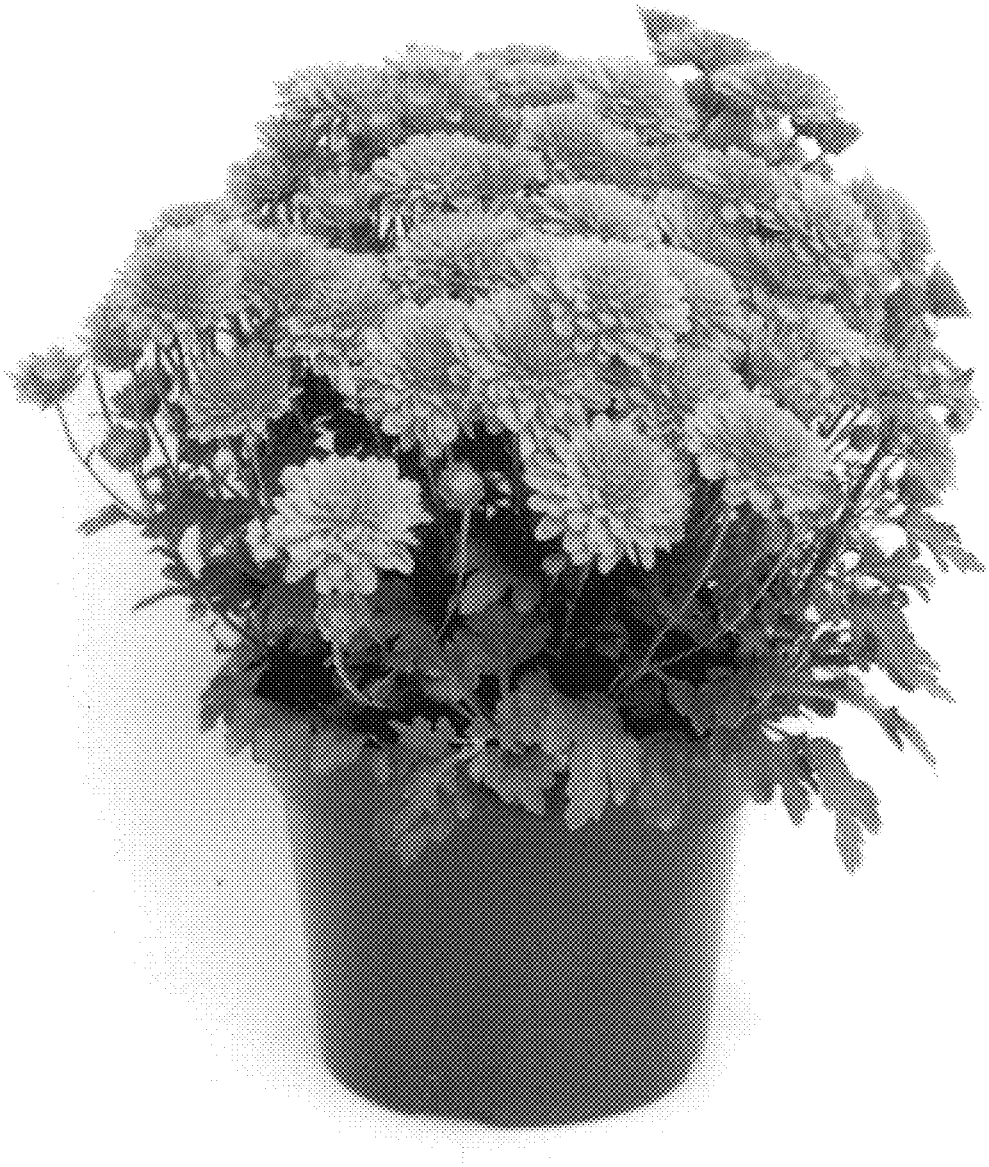

* * * * *